United States Patent
Chen

[11] Patent Number: 6,040,900
[45] Date of Patent: Mar. 21, 2000

[54] COMPACT FIBER-OPTIC ELECTRONIC LASER SPECKLE PATTERN SHEAROGRAPHY

[75] Inventor: Xiaolu Chen, Saline, Mich.

[73] Assignee: Cybernet Systems Corporation, Ann Arbor, Mich.

[21] Appl. No.: 08/886,317

[22] Filed: Jul. 1, 1997

Related U.S. Application Data
[60] Provisional application No. 60/020,750, Jul. 1, 1996.

[51] Int. Cl.[7] ........................................ G01B 9/02
[52] U.S. Cl. ............................ 356/35.5; 356/356
[58] Field of Search .......................... 356/358, 356, 356/345, 353, 401; 434/17

[56] References Cited

U.S. PATENT DOCUMENTS

| | | | |
|---|---|---|---|
| 3,445,855 | 5/1969 | Grant | 346/1 |
| 3,545,259 | 12/1970 | Grant | 73/60 |
| 3,645,129 | 2/1972 | Grant | 73/67 |
| 4,125,314 | 11/1978 | Haskell et al. | 350/3.6 |
| 4,139,302 | 2/1979 | Hung et al. | 356/32 |
| 4,171,794 | 10/1979 | Haskell et al. | 251/50.1 |
| 4,392,745 | 7/1983 | Wright et al. | 356/348 |
| 4,425,039 | 1/1984 | Grant | 356/35.5 |
| 4,620,223 | 10/1986 | Haskell et al. | 358/107 |
| 4,650,302 | 3/1987 | Grant | 351/206 |
| 4,682,892 | 7/1987 | Chawla | 356/353 |
| 4,690,552 | 9/1987 | Grant et al. | 356/35.5 |
| 4,702,594 | 10/1987 | Grant | 356/35.5 |
| 4,832,494 | 5/1989 | Tyrer | 356/354 |
| 4,887,899 | 12/1989 | Hung | 3356/35.5 |
| 5,007,738 | 4/1991 | Grant | 356/347 |
| 5,065,331 | 11/1991 | Vachon et al. | 364/508 |
| 5,082,366 | 1/1992 | Tyson, II et al. | 356/35.5 |
| 5,094,528 | 3/1992 | Tyson, II et al. | 356/345 |
| 5,121,148 | 6/1992 | Windeler et al. | 354/152 |
| 5,146,289 | 9/1992 | Newman | 356/359 |
| 5,641,288 | 6/1997 | Zaenglein, Jr. | 434/19 |

OTHER PUBLICATIONS

Brown, G. C. and Pryputniewicz, R. J. (1993). Measurement of young's modulus on thin films under static and dynamic loading conditions. SPIE vol. 2004 Interferometry VI: Applications.

Chiang et al., "Laser Speckle Interferometry for Plate Bending Problems", Applied Optics, vol. 15, No. 9, pp. 2199–2204, Sep. 1976.

Chiang et al., ; "Stress Analysis of In–plane Vibration of 2–D Structure by a Laser Speckle Method", Applied Optics, vol. 19, No. 16, Aug. 15, 1980; pp. 2705–2708.

Chatters, T., Pouet, B. and Krishnaswamy, S. (1993). Non-destructive testing of adhesively bonded structures using synchronized pressure stressing. SPIE vol. 2001 Nondestructive Inspection of Aging Aircraft. pp. 236–247.

Hung et al, "Image–Shearing Camera for Direct Measurement of Surface Strains", Applied Optics, vol. 18, No. 7, (Apr. 1, 1979) pp. 1046–1051.

Holownia, B. P. (1988). Examination of adhesive joints using electronic speckle pattern interferometry. Plastics and Rubber Processing and Applications 9, pp. 203–208.

(List continued on next page.)

*Primary Examiner*—Frank G. Font
*Assistant Examiner*—Tu T. Nguyen
*Attorney, Agent, or Firm*—Gifford, Krass, Groh, Sprinkle, Anderson & Citkowski, PC

[57] ABSTRACT

Material defects and damage are detected and evaluated by stressing the material while looking for flaw-induced anomalies. In one embodiment, a thermal stressing unit is used to provide a slight temperature difference between a localized region and surrounding areas, with the change in temperature being used to reveal the defects and damage using a fringe pattern generated through the interference between two coherent laser beams. A sensor head and a head-mounted display (HMD), interfaced to a computer, power supply, and control electronics are used to measure the derivative of out-of-plane displacement with respect to an image shearing direction so as to generate a display of the fringe pattern, preferably in three dimensions through a displacement or depth map.

8 Claims, 5 Drawing Sheets

OTHER PUBLICATIONS

Chen, X. L. and Cloud, G. L. (1994). Nondestructive evaluation of composites using ESPI and gravity loading. Proc. 1994 SEM Spring Conference and Exhibits, Baltimore, Maryland. Jun., 1994.

Hariharan, "Speckle–Shearing Interferometry: A Simple System", Applied Optics, vol. 14, No. 11, (Nov. 1975) p. 2563.

Duffy, "Measurement of Surface Displacement Normal to the Line of Sight", Eaptl. Mech. pp. 378–384, Sep. 1974.

Höfling, R., Aswendt, P., Totzauer, W. and Jüptner, W. (1991). DSPI: A tool for analyzing thermal strain on ceramic and composite materials. SPIE vol. 1508, Industrial Applications of Holographic and Speckle Measuring Techniques, pp. 135–142.

Hung et al, "Speckle–Shearing Interferometric Technique: a Full–Field Strain Gauge", in Applied Optics, vol. 14, No. 3, Mar., 1975, pp. 618–622.

Hung, "Shearography: A New Optical Method for Strain Measurement and Nondestructive Testing", Optical Engineering, May–Jun. 1982, pp. 391–395.

Conley, E. and Genin, J. (1990). Application of speckle metrology at a nuclear waste repository. SPIE vol. 1332, Optical Testing and Metrology III: Recent Advances in Industrial Optical Inspection, pp. 798–801.

Koliopoulos, "Radial Grating Lateral Shear", Applied Optics, vol. 19, No. 9, pp. 1523–1528, May 1980.

Kwon, O.; "Infrared Lateral Shearing Interferometers", Applied Optics, vol. 19, No. 8 (Apr. 15, 1980) pp. 1225–1227.

Deaton, J.B. Jr. and Rogowski, R.S. (1993). Applications of electronic shearography for the inspection of airskin structures. SPIE vol. 2001 Nondestructive Inspection of Aging Aircraft. pp. 224–235.

Lokberg, "Use of Chopped Laser Light in Electronic Speckle Pattern Interferometry", Applied Optics, vol. 18, No. 14, pp. 2377–2384, Jul. 1979.

Macovski, A., Ramsey, S. D. and Schaefer, L. F. (1971). Time–lapse interferometry and contouring using television system. Applied Optics, vol. 10, No. 12, pp. 2722–2727.

Hung, Y. Y. and Taylor, C. E, "Measurement of Slopes of Structural Deflections by Speckle–Shearing Interferometry", in Experimental Mechanics, vol. 14, No. 7, pp. 281–285. Jul. 1974.

Maji, A. K. and Wang, J. (1992). Fracture mechanics of a tension–shear microcrack in rocks. Experimental Mechanics, pp. 190–196, Jun.

Maji, A. K., Wang, J. L. and Lovato, L. (1991). Electronic Speckle Pattern Interferometry for fracture mechanics testing. Experimental Techniques, pp. 19–23.

Nokes, J., Cloud, G., Chen, X. and Wede, H. (1995). Interferometric Inspection of Composite Overwrapped Pressure Vessels. 1995 SEM Spring Conference, Grand Rapids, Michigan, Jun. 12–14.

Mallick et al, "Spatial Differentiation by a Lateral Shear Interferometer", Applied Optics, vol. 11, No. 2, (Feb. 1972), pp. 479–480.

Murty et al., "Liquid Crystal Wedge as a Polarizing Element and Its Use in Shearing Interferometry", Optical Engineering, vol. 19, No. 1, (Jan./Feb. 1980) pp. 113–115.

Preater, R. and Swain, R. (1993). A preliminary assessment of the requirements to transfer in–plane ESPI to an industrial spinning pit facility. SPIE vol. 2004 Interferometry VI: Applications. pp. 142–149.

Nakadate, S., Yatagai, T. and Saito, H., "Digital Speckle––Pattern Shearing Interferometry", Applied Optics, vol. 19, No. 24, Dec. 15, 1980, pp. 4241–4246.

Thinh et al., "Speckle Method for the Measurement of Helical Motion of a Rigid Body", Optica Acta, vol. 24, No. 12, pp. 1171–1178, Dec. 1977.

Ratnam, M. M., Evans, W. T. and Tyrer, J. R. (1992). Measurement of thermal expansion of a piston using holographic and electronic speckle pattern interferometry. Optical Engineering, vol. 31, No. 1, pp. 61–69.

Safai, M. (1992). Real–time shearography of silicone rubber bonds. Materials Evaluation, pp. 698–701, Jun.

Safai, M. (1993). Nondestructive evaluation of aircraft fuselage panels with electronic shearography. SPIE vol. 2066 Industrial Optical Sensing and Metrology, pp. 20–25.

bull's-eye · butterfly · fringe discontinuites · abrupt fringe curvature changes · sudden fringe density changes

COMPACT FIBER-OPTIC ELECTRONIC LASER SPECKLE PATTERN SHEAROGRAPHY

REFERENCE TO RELATED APPLICATION

This application claims priority of U.S. provisional application Ser. No. 60/020,750, filed Jul. 1, 1996, the entire contents of which are incorporated herein by reference.

FIELD OF THE INVENTION

The present invention relates generally to material characterization and, in particular, to a thermal stressing technique which uses electronic shearography to detect flaws or defects in materials or objects.

BACKGROUND OF THE INVENTION

Speckle shearography dates back to the early 1970s. An electronic version of speckle shearography, ES, was developed in 1980 and, since that time, ES has been applied to the study of many different phenomena, primarily in research laboratories. Such applications range from the nondestructive inspection of aircraft to vibration analysis, materials characterization, and electronic packaging study. ES has also been used to locate subsurface disbonds between silicone rubber and the substrate of missiles, to detect disbonds in aircraft fuselage panels, to inspect airskin structures, and in Q-switched pulsed lasers (which are complex and expensive).

The NDI (nondestructive inspection/evaluation) methods most widely used in industry are ultrasonics, eddy-current measurement, and x-radiography. The ultrasonic techniques are used to detect flaws by measuring the response to an ultrasonic stress wave. However, due to the point-by-point or line-by-line scanning procedures involved, the ultrasonic method is typically slow. A medium, such as water or gel, is usually required to transfer the ultrasound energy from the transducer into the material, which is inconvenient in some cases.

X-radiography relies on the differential absorption or scattering of x-ray photons as they pass through a material. Flaws that either allow more x-ray photons to pass or that absorb or scatter the photons can be imaged if the effect is sufficiently pronounced. The molecules in many polymer composites are usually of low atomic weight nuclei, and hence the absorption of x-rays is low and contrast is usually poor, especially for a thin plate. Eddy-current measurement is only applicable to metallic materials. Furthermore, none of these methods relate flaw detection to the stress/strain states of a test object in any fundamental way. Therefore, how a detected flaw affects the performance of a particular component cannot be revealed by current detection processes.

Unlike these traditional methods, loading (stressing) is an essential part of NDI processes based upon ES. The loading provides an important connection between the detected flaws and the effect of the flaws on the integrity and strength of the structures under test.

Ultrasonic and x-ray technologies are good at determining the geometry and detailed location of the flaws, especially the internal flaws in a structure. Unfortunately, neither of these methods relate the detection to the effect of the flaws on material integrity or strength. Furthermore, for inspection of a large area, these techniques are slow and costly. Although ES is most sensitive to surface and subsurface flaws, internal flaws can also be detected from their induced "disturbances" on the surface when an appropriate stressing technique is used.

Among all NDI techniques discussed, laser interferometry, including holographic interferometry and ES, are the only tools which can detect flaws through the direct measurement of a material's strength-related parameters such as deformation/displacement or strain. These techniques also offer the opportunity for directly assessing the actual effects of the detected damage on the structures. Laser interferometry techniques are highly sensitive to a wide variety of flaws and can inspect a large area at fast speed.

SUMMARY OF THE INVENTION

According to the present invention, material defects and damage are detected and evaluated by stressing the material while looking for flaw-induced anomalies in a fringe pattern generated by the interference between two coherent laser beams and electronic image processing. In terms of apparatus, the system includes a sensor head and a head-mounted display (HMD), interfaced to a computer, power supply, and control electronics. In one embodiment, the sensor head contains a thermal stressing unit and electronic shearography (ES) optics which measures the derivative of out-of-plane displacement with respect to an image shearing direction. In operation, the thermal stressing unit is used to provide a slight temperature difference between a localized region and surrounding areas, with the change in temperature being used to reveal the defects and damage.

DETAILED DESCRIPTION OF THE INVENTION

Figure 1:
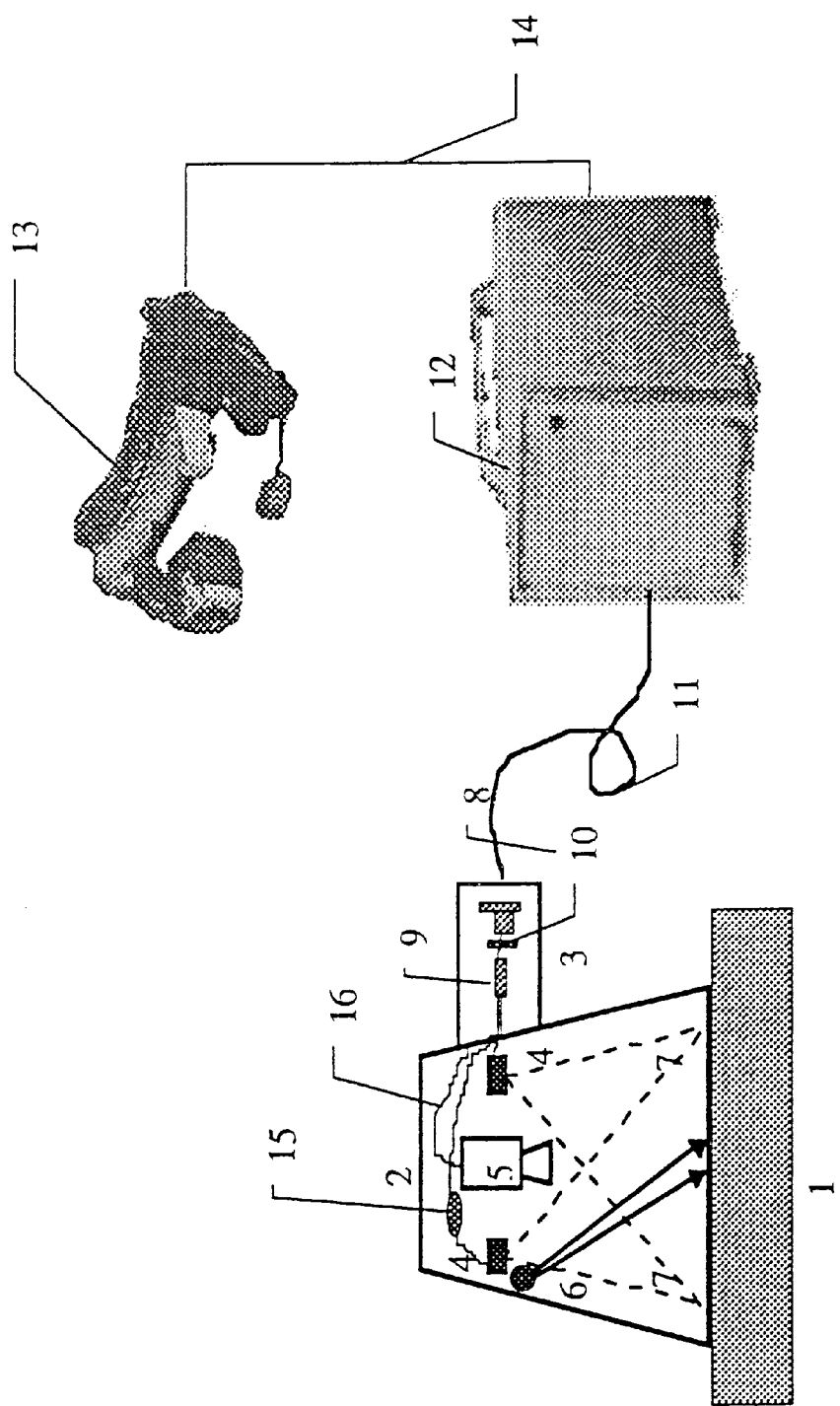
FIG. 1 is an overall view of apparatus according to the invention.

As shown in FIG. 1, a system according to the invention includes a sensor head, a head-mounted display (HMD), and an electronic subsystem which contains a computer, power supply, and control electronics. The sensor head contains a thermal stressing unit and electronic shearography (ES) optics which measure the derivative of out-of-plane displacement with respect to the direction of image shearing.

The thermal stressing unit is used to provide a slight temperature difference between a localized region and its surrounding areas. Alternative loading methods such as object bending or pressurization can also be used. The temperature change reveals the defects and damage in the materials. This invention provides a means for large-area nondestructive inspection and evaluation of materials and structures and, in particular, may be used in the characterization of very large vehicles and vessels such as aircraft. In nondestructive inspection/evaluation applications, the apparatus and methods may be used to detect and evaluate defects and damage within materials. The defects and damage are detected and evaluated by stressing the materials and looking for flaw-induced anomalies in the fringe pattern. The fringe pattern is generated by the interference between two coherent laser beams resulted from the image shearing lens (FIG. 2) and electronic image processing. The sensor head is designed to be hand-held.

The results which represent surface deflections under stress load are displayed on a miniature monitor inside the HMD, preferably as a color-coded image, wherein colored areas are based on stress concentration. The HMD is lightweight, and is worn on the head of the operator.

The compact electronic subsystem includes a microcomputer, a power supply, a frame grabber for image acquisition, and a piezo-electric transducer (PZT) controller for implementing phase-stepping with respect to quantitative fringe analysis.

Figure 2:
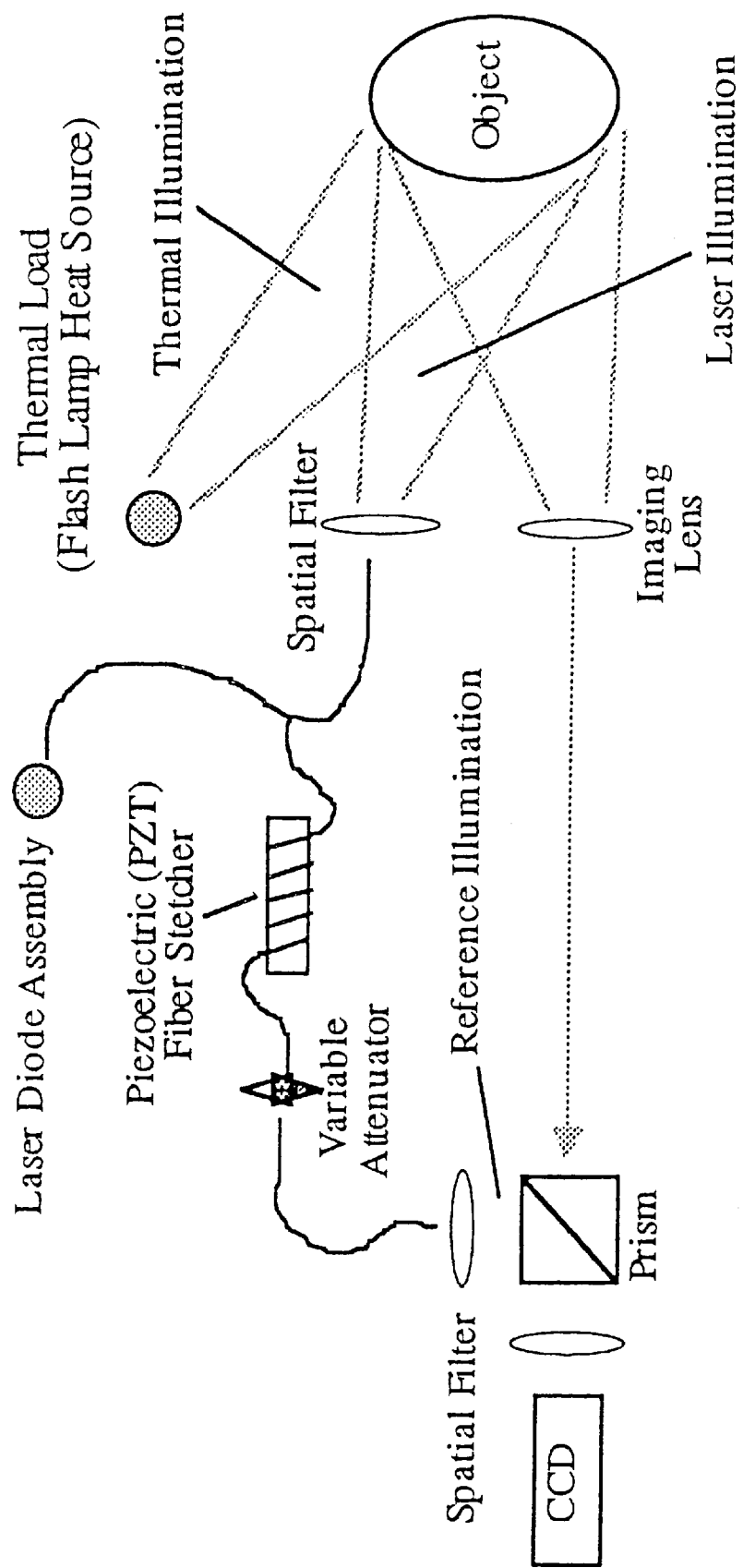
FIG. 2 is a schematic diagram of the electronic shearography optics mounted inside a sensor head.

Electronic shearography measures the derivative of the out-of-plane displacement with respect to the direction of image shearing. ES is a 'common-path' interferometry, which is much less susceptible to the influence of rigid-body motion, as compared to other interferometries. An ES employs an image-shearing camera which produces a pair of laterally shifted images in the image plane, preferably using a CCD array. FIG. 2 shows the ES optics using Michelson interferometer construction.

In ES, the interferometric fringes formed are a measure of the amount of surface deformation between two different states of the object under test. The comparison may be between two deformed (stressed) states or between a deformed state and an undeformed (unstressed) state. The method of stressing the object is critical, because the sensitivity of different types of flaws to different loading or stressing methods is different.

The reaction to stressing is a function of physical and material properties with respect to the loading method. Normally, the fringes, or deformation contours, on the test object are continuous and smooth. But in the regions of flaws or damage, the response of the surface to the stress is often different, and the flaws and damage disturb the strain field, causing anomalies in the fringe pattern. Although ES normally detects the surface and subsurface flaws, these flaws are believed to be the most responsible for early fatigue failures. The flaws and damage which affect the structure the most may be detected by employing the loading type which simulates the working condition of the product. These defects may be cracks, voids, debondings, impact damage, inhomogeneous material properties, delaminations, fiber breakage, matrix cracking and so on.

Figure 3:
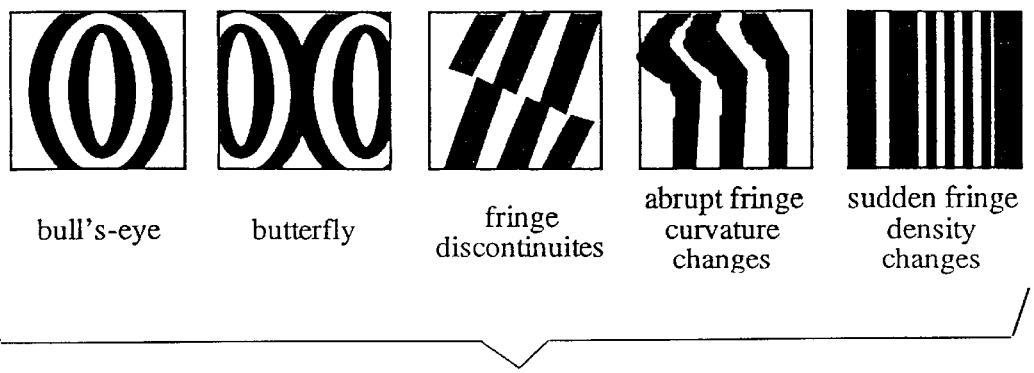
FIG. 3 shows typical defect presentation.
Figure 4:
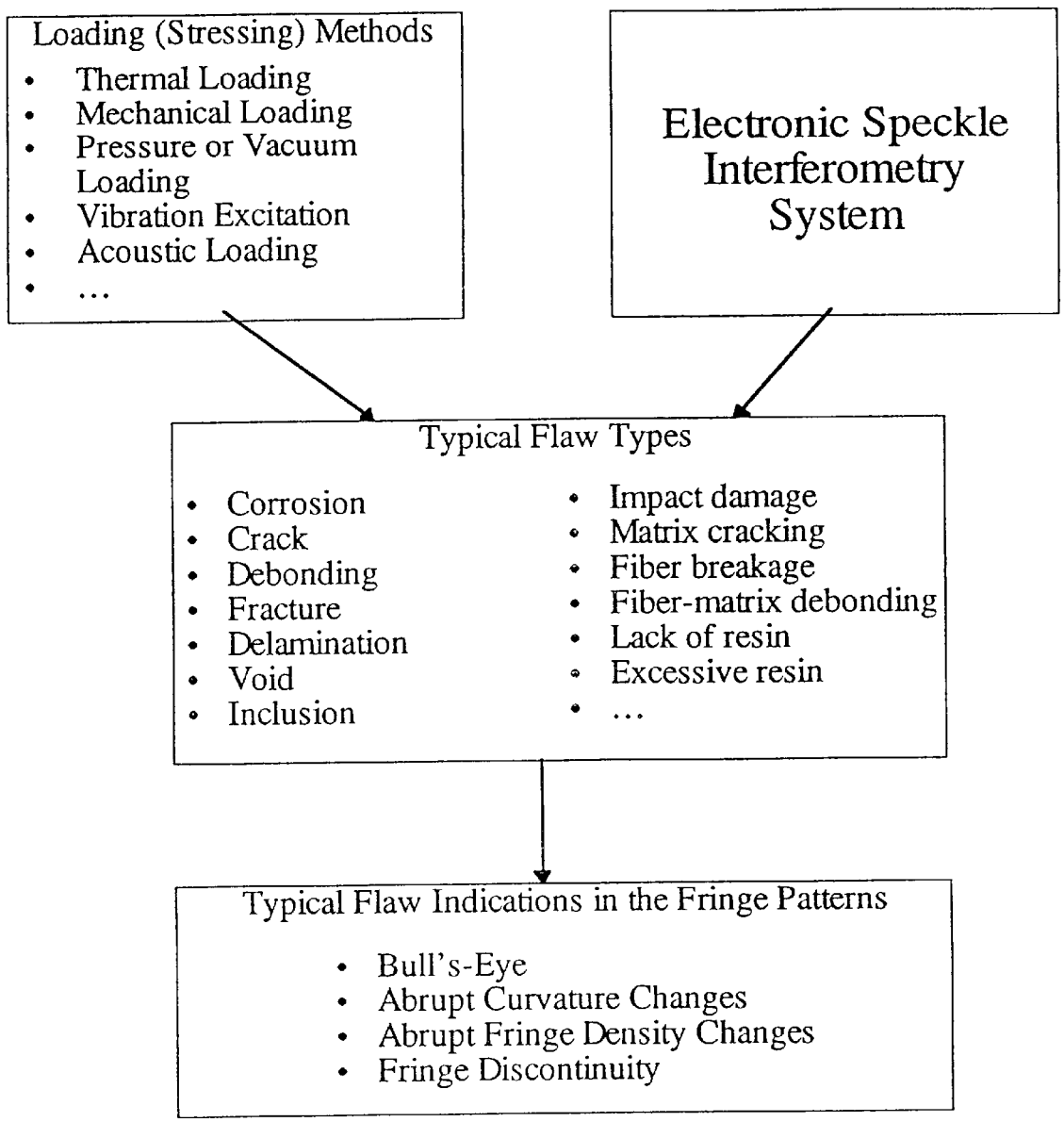
FIG. 4 is a flowchart of damage and flaw detection types.

Such flaws or damage are normally manifest in the fringe pattern as fringe anomalies such as "bull's-eye," "butterflies," fringe discontinuities, abrupt fringe curvature changes, or sudden fringe density changes, as shown in FIG. 3. Loading techniques should therefore be designed so that flaws and damage can be revealed as distinctly as possible, and so that the ideal loading may be the one which simulates the actual working condition of the component. Automatic pattern recognition methods combined with a knowledge-based approach can be used for the detection and classification of anomalous fringe patterns. The principle of damage and flaw detection is outlined in the flow chart of FIG. 4

The key to successful NDE using ES is to select an effective stressing technique that will reveal defects by inducing localized surface deformation. Although the system described herein employs a thermal stressing unit, the object under test can also be slightly or mildly stressed in other ways, including mechanical stressing, thermal excitation, pressurization, vacuum, and acoustic or mechanical vibration. The method employed would depend upon the object itself, the type of defect to be detected, and the accessibility of the object.

For each loading method, there are a number of ways to carry it out. Thermal stressing is convenient for loading over large surface areas without access to anything other than the front surface face, where the surface is thermally illuminated. For pressure vessels, internal pressurization is a suitable loading method. For plates or some part types, compression or pulling can be utilized. For plates or beams, bending may be a suitable loading method.

Referring to the ES setup shown in FIG. 2, the thermal load illuminates the object surface to create a build-up of heat. Under heating, the surface expands and loads or pressurizes the surface material. In the presence of an internal defect, the surface material is weakened, and will buckle in or buckle out a small amount. This causes changes in surface tangent angle and displacement, which can be measured using laser interferometric means, namely electronic shearography.

In a preferred embodiment a diode assembly, including a coherent laser diode and focusing/beam forming optics, begins the defect imaging process by projecting coherent light onto the object surface to be imaged. The surface is imaged through a programmably controlled image shearing optical assembly which incorporates a shearing optic, an adjustable image shearing mirror, and a program-controlled PZT mirror (piezo-electric device actuated mirror). The sheared image is formed by imaging to a standard charge-coupled-device (CCD) camera device.

The imaging system can be operated in at least two modes. In a fast mode, the phase-stepping technique, controlled by the PZT, is not activated, which allows an operator to rapidly perform large-area inspection(s). In this mode, real-time electronic image subtraction and image enhancement are performed to generate fringe patterns to reveal flaws in the form of small surface displacements. Also in this mode, flaws show up as irregularities in the smooth fringe pattern. These irregularities are typical of specific flaw types, so that the operator can classify probable flaws by viewing them directly. However, it may be difficult to convert the flaw images into quantitative display measurements in this mode. Phase deconvolution methods may be used to convert from fringe pattern to phase displacements to actual displacements, but such methods are relatively inaccurate and may be ambiguous in phase deconvolution for many patterns.

In the slower mode, a phase-stepping technique is activated. The operator can zoom into the localized region containing flaws, and conduct an detailed quantitative evaluation of the flaws. In this mode, a set of images will be produced using a phase-stepping technique and computed to generate quantitative map of the derivative of the displacement.

Phase stepping is implemented by shifting the shearing system very small amounts using the PZT actuator. With three shifted images, it is possible to compute phase displacement and then actual surface displacement directly in closed form. Then, with an appropriate phase unwrapping algorithm, displacements can be found and these results can be stored in a database and retrieved for later use in quantitative defect assessment.

Figure 5:
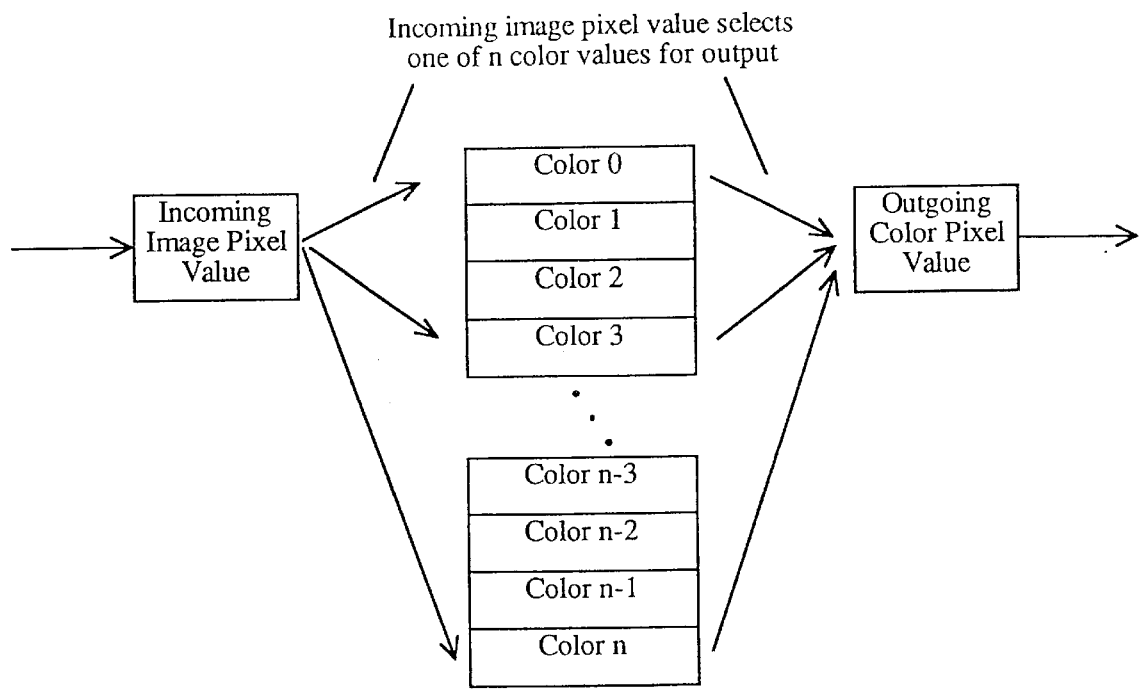
FIG. 5 is a color mapping for display purposes.

After defect/clear image formation, the image is presented to an operator or automated system for assessment. When presented to an operator, typically four image forms are available. The first is the direct view of the surface (i.e., without any fringe processing). This view can help an operator register other views to features on the surface under normal viewing conditions. This view also allows for the detection of defects at the object surface (no visibility inside the surface is possible). This "plain view" can be enhanced through edge detection, which enhances small defects, and can be used as an overlay to a normal image with color coded edge strength, that is, the image can be spatially differentiated and mapped into a color code through a pallet of colors associated with edge strength level. FIG. 5 shows this process of mapping a signal scale into a color map for improved operator perception.

The next image available is the fringe image formed by the electronic shearography sensor, which shows laser interference patterns. These patterns can be smoothed and also mapped through a color look-up pallet to enhance operator perception of the fringe patterns.

Finally, in the slow mode, three or more fringe images, which are phase shifted (via the PZT) by known amounts from each other. These can be used to compute phase-map images which look effectively like the fringe images, but represent known displacements. By phase unwrapping and scaling these phase images, true displacement images can be computed. Again the phase map image and the true display images can be color coded to enhance operator perception of defects.

Figure 6:
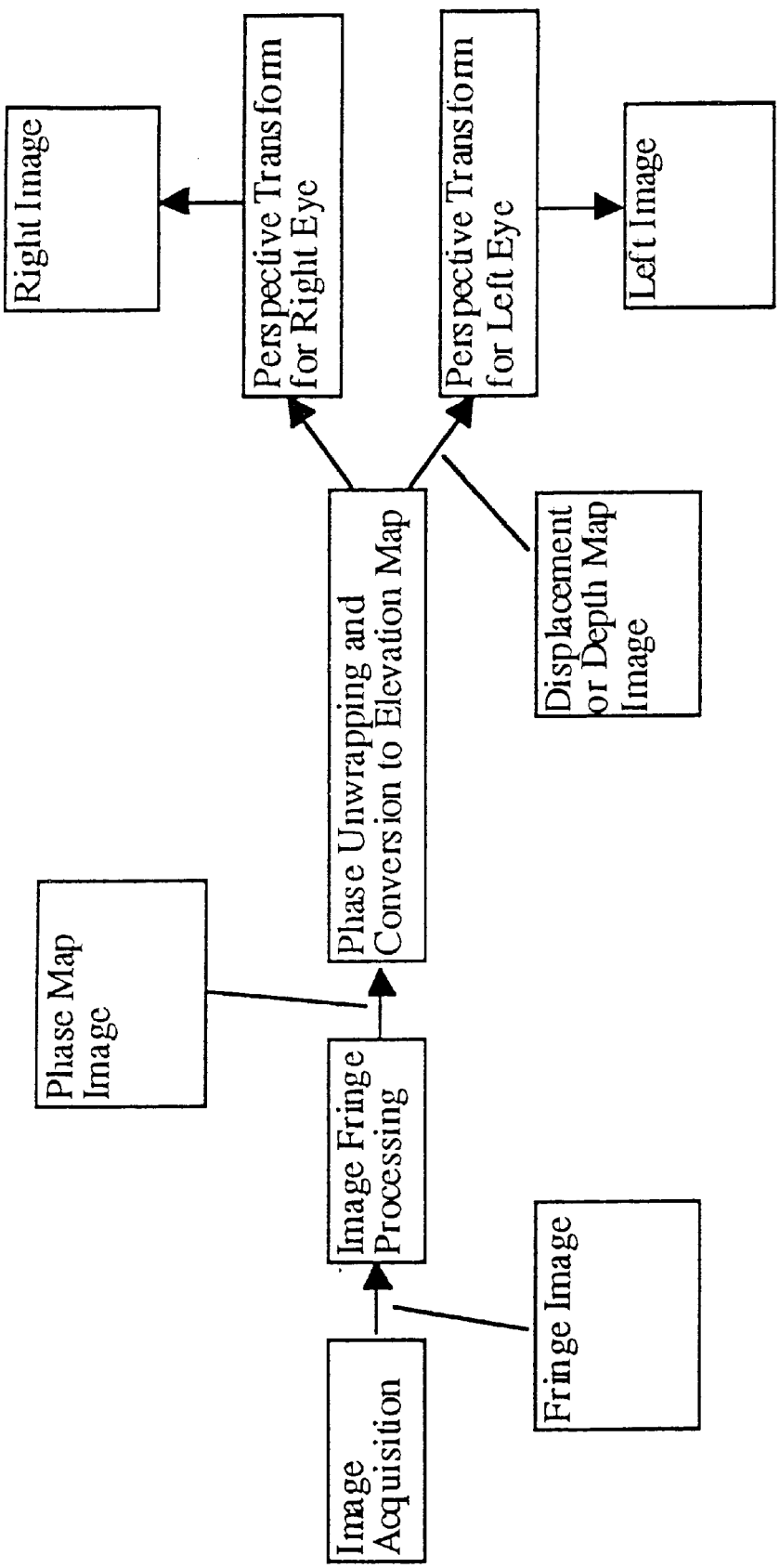
FIG. 6 illustrates three-dimensional view generation according to the invention.

All of these images can either be displayed on a conventional display device such as a CRT or flat panel, but can also be directly present to the operator through an HMD, such as a helmet or head-mounted display. This may be particularly interesting in the case of true displacement images, as these represent a true three-dimensional representation, and can thus be transformed into alternative perspective views through 3D computer graphics. This allows the operator to be presented with two alternative images, one for the right eye and one for the left eye, thus generating a three-dimensional perception of a microscopic defect for the benefit of an operator, as shown in FIG. 6.

That which is claimed is:

1. A system for detecting defects and damage in an object, comprising:

a thermal stressing unit operative to provide a slight temperature differential between a localized region and a surrounding area of the object;

two coherent laser beams directed toward the object, enabling the objects to interfere with one another within the localized region;

electronic shearography optics having a field of view which includes the localized region, the optics being operative to measure the derivative of out-of-plane displacement with respect to an image shearing direction so as to generate a fringe pattern characteristic of flaw-induced anomalies; and a display device, operatively coupled to the electronic shearography optics, upon which to view the fringe pattern.

2. The system of claim 1, wherein the display device forms part of a head-mounted display.

3. The system of claim 2, further including a programmed controller interfaced to the head-mounted display to generate a three-dimensional view of the fringe pattern.

4. The system of claim 3, wherein the controller is operative to perform the following functions:

a) convert the fringe pattern into a phase-map image;

b) unwrap the phase of the phase-map image to generate an elevation map; and c) present right and left perspective transforms to the right and left eyes of a viewer through the head-mounted display.

5. A method of detecting defects and damage in an object, comprising the steps of:

thermally stressing a localized region of the object;

directing two coherent laser beams directed toward the object while it is thermally stressed, such that the beams interfere with one another within the localized region;

viewing the localized region through electronic shearography optics to measure the derivative of out-of-plane displacement with respect to an image shearing direction so as to generate a fringe pattern characteristic of flaw-induced anomalies; and viewing the fringe pattern on a display device.

6. The method of claim 5, wherein the step of viewing the fringe pattern on a display device includes viewing the fringe pattern through a head-mounted display.

7. The method of claim 5, further including the step of generating a three-dimensional display of the fringe pattern.

8. The system of claim 7, further including the steps of:

a) converting the fringe pattern into a phase-map image;

b) unwrapping the phase of the phase-map image to generate an elevation map; and c) presenting right and left perspective transforms to the right and left eyes of a viewer through the head-mounted display.

* * * * *